(12) United States Patent
Ballester (10) Patent No.: US 8,499,393 B2
(45) Date of Patent: Aug. 6, 2013

(54) LOADING WHARF

(75) Inventor: Miguel Angel Iglesias Ballester, Barcelona (ES)

(73) Assignee: Amiserru, S.L., Barcelona (ES)

( * ) Notice: Subject to any disclaimer, the term of this patent is extended or adjusted under 35 U.S.C. 154(b) by 0 days.

(21) Appl. No.: 13/130,184

(22) PCT Filed: Dec. 10, 2008

(86) PCT No.: PCT/ES2008/000770
§ 371 (c)(1),
(2), (4) Date: May 19, 2011

(87) PCT Pub. No.: WO2010/066915
PCT Pub. Date: Jun. 17, 2010

(65) Prior Publication Data
US 2011/0225744 A1    Sep. 22, 2011

(51) Int. Cl.
*E01D 1/00* (2006.01)
(52) U.S. Cl.
USPC .......................................... 14/71.1; 52/173.2
(58) Field of Classification Search
USPC ................... 14/71.1, 71.5; 52/173.2
See application file for complete search history.

(56) References Cited

U.S. PATENT DOCUMENTS

| | | |
|---|---|---|
| 4,478,268 A | 10/1984 | Palmer |
| 4,825,607 A | 5/1989 | Frommelt et al. |
| 5,473,846 A | 12/1995 | Giuliani et al. |
| 6,170,204 B1 | 1/2001 | Strobel et al. |
| 7,757,442 B2 * | 7/2010 | Hoffmann et al. ........... 52/173.2 |
| 2004/0261335 A1 | 12/2004 | Eungard |
| 2007/0283636 A1 | 12/2007 | Bernacki et al. |

* cited by examiner

*Primary Examiner* — Gary Hartmann
(74) *Attorney, Agent, or Firm* — Leason Ellis LLP (57) ABSTRACT

A loading wharf includes a compact structure secured to the perimeter of an access opening formed in a wall of a building. The compact structure defining between the inner and outer faces of the wall, an intermediate space for placement of protective members and a folding ramp both of which move between an operational position in which protective members and ramp project from the intermediate space towards the outside, in order to interact with the body or trailer of the vehicle to be loaded or unloaded, and a non-operational position in which the protective members and ramp are positioned inside the intermediate space and are oriented vertically. The compact structure includes, corresponding to the outer and inner faces of the wall, frames for the mounting of an exterior closure door and of an interior door.

21 Claims, 9 Drawing Sheets

LOADING WHARF

OBJECT OF THE INVENTION

This present invention refers to a loading wharf for industrial warehouses, of the type which has a folding ramp intended to make a bridge between the warehouse and the body or trailer to be loaded or unloaded, protective means for the closure of the space between the warehouse and the body or trailer of the lorry during the loading and unloading operations, an external door to close off the space when same is not in use and an internal door, preferably rapid, to keep the opening closed whilst the linking of the lorry trailer to the opening is carried out.

BACKGROUND TO THE INVENTION

At the present time it is common for industrial units to have one or more loading and unloading wharves for materials.

These wharves are arranged connecting to the threshold door of the access from the outside to the inside and include a ramp that makes the passage for the fork lift trucks or other vehicle loaders between the warehouse and the body or trailer of the lorry.

The ramp is generally arranged on the inside of a pit that goes into the space on the inside of the warehouse, the devices to activate the ramp being housed in said pit, mainly hydraulic cylinders, equipment to provide hydraulic pressure and control devices. This ramp is jointed on the lower part of the door or in a slightly emerging edge and which extends over the pit, which is more or less exposed.

These loading wharves also have some temporary protective means on the outside of the access door that are adaptable to the shape of the body of the lorry and which close the sides and top space that there is between the door of the wharf and the lorry.

The wharves of this type have some problems in use amongst which the one that stands out is the accumulation of dirt and waste in the pit, generated by the cleaning in the areas in which they are installed on entering into the space of same, allowing (due to the tolerances of the ramp with the floor for their possible movement) the passage of dust, insects and even rodents though these spaces.

In turn, the external protective means is shaped by some sheet rubber, canvas or similar elements, that are permanently exposed to the elements, on the external façade of the unit, being able to be damaged by the action of the wind or by vandalism if they are in poorly protected enclosures.

DESCRIPTION OF THE INVENTION

The loading wharf, object of this invention, presents some technical peculiarities that provide a series of advantages amongst which the following can be highlighted: Its installation is easier, occupying minimal space, without the need to carry out works for the construction of a pit, the availability of a flat and continuous floor on the inside of the warehouse, making cleaning and appropriate hygienic conditions easier, to provide a greater protection to the protective means when the loading wharf is not being used, to eliminate the problem of the build up of dirt in the ramp installation area, to enable the effective closure of the loading wharf when it is non-operational, with all of the operational elements contained on the inside and enabling the inter-connection of all of the openings to each other by means of the union of said structures via pipes through which the pre-installation of electrical, pneumatic and hydraulic supplies in addition to telephone and data lines can be made.

According to the invention the loading wharf includes a compact structure fixed into the entirety of the access opening to the warehouse and which marks out an intermediate space for the placement of the protective means and the folding ramp between the internal and external faces of the wall, with the possibility of movement between an operating position in which it projects from the stated intermediate space towards the outside to interact with the body or trailer of the lorry to be loaded or unloaded and in a non-operational position in which said means and ramp are positioned inside said intermediate space. Said compact structure includes a connection with the internal and external wall and some frames for the assembly of an external closure door on the outside of the warehouse, preferably of the rapid-opening type, that establishes the closure on the ground or floor level of the warehouse.

According to the invention, the intermediate space has: a lower area, located on the outside of the warehouse, for the housing of the platform behind the lorry or safety mechanisms intended to prevent the movement of the lorry during the loading and unloading operations; a lower intermediate area located below the inner level of the warehouse for the movement of the platform; an upper intermediate area, made flush with the inner level of the warehouse for the housing of the protective means and the ramp; and an upper area forming a housing for the gathering up of the outer and inner doors in the open position.

According to the invention the compact structure can be made into a single pre-assembled module, that takes in the total height of the access opening to the warehouse, from the outer lower level of the warehouse (running surface of the lorries) up to the end of the body of the upper area (above the lintel) if there is one or the lintel itself in the event of there not being a body, or in two independent modules; one lower module that includes the lower area and the lower intermediate area, this being, up to the internal level of the warehouse, and an upper module that includes the upper intermediate and the upper areas.

This second arrangement allows the lower and upper modules to be able to be supplied separately, so that they can be integrated in successive phases of the warehouse construction, avoiding unnecessary risks of deterioration of the upper module during the stated construction phases.

The protective means include two folding side pieces and an upper roof, the stated protective means and the levelling ramp being gathered up by some actioning devices that allow for the movement between the stated operational and non-operational positions. Said actioning means can be made up of motorised axles, hydraulic cylinders or any other, as they do not alter the essence of the invention.

In one embodiment of the invention, the inner and outer frames define some channelling for the controls of the doors themselves and for the passage of the electrical supply cables for the differing elements and auxiliary services, such as battery chargers for pallet trucks, signalling elements, light switches or means of communication. In this way the control or supply cables are prevented from being exposed and being able to be accidentally damaged during the loading and unloading operations.

In one embodiment of the invention, the sides of the protective means are assembled on both vertical turning axes, close to the inner sides of the compact structure, the upper roof on an upper horizontal turning axis and the ramp on a turning axis.

According to the invention, in the non-operational position both the sides and the roof of the protective means in the same way as the ramp are suitably arranged in a vertical manner on the inside of the intermediate opening set by the outer and inner doors and by the compact structure.

In one embodiment of the invention, there are some means of signalling on the opposing sides of the external frame to make the centring and approach of the vehicle to the wharf easier. These signalling devices include two sets of signals making horizontal and vertical signalling lights of differing colours on each side and which are easily visible using the rear view mirrors of the vehicle. When the lorry correctly approaches the loading wharf, the driver can see the signal lights in the two rear view mirrors and at the moment in which if the lorry deviates from an appropriate path towards one side the driver immediately sees a different number of signals on the left and right, warning in an unmistakable manner which side of the rear of the vehicle is wrong.

In one embodiment of the invention the vertical signal alignments are directed by some sensors that detect the position of the rear end of the lorry in regard to the loading wharf, said signals providing some visual information on the distance and correct position or of the excessive distance of the lorry from the loading wharf.

The ramp has the same width as that between the sides of the protective means in the operational position, with the exception of the support toe on the lorry, which has a narrower width, preventing the making of grooves or holes between same.

According to the invention in the operational position of the loading wharf the platform and protective means remain joined by some inter-connecting devices, acting as an adjustable unit for the variations in height of the body of the lorry brought about during the loading and unloading as a result of the weight variation borne by same; preventing rubbing between the lorry and the protective means during said loading and unloading operations.

The successive wharves can be inter-connected by means of built in tubes or pipes that can join the housings enabling the electrical, pneumatic, telephone and data installations to be made that are necessary for the inter-connection of all of the necessary components in the loading openings meaning that the inner walls remain clean, free of pipes and channelling that could affect or reduce the cleaning of same.

According to the invention, the inner floor of the warehouse is smooth and does not have any grooves or cuts that allow the accumulation of dirt and the communication areas between the inside and outside of the warehouse thus making the floor more hygienic and easier to clean.

In one variation of an embodiment of the invention, the external door of the wharf has an upper and a lower part that can fold on both horizontal axes said panels respectively making the roof of the protective means and an additional closure for under the level of the ramp.

In a second variation of an embodiment of the invention, the external door is made up from two side folding panels on both vertical axes, which additionally make the sides of the protective means and by an upper folding panel on a horizontal axis, which overlaps the side folding panels and in addition makes the roof of the protective means.

In a variation of the invention, the compact structure has a smaller width than the opening to the warehouse and has some lateral projections that easily cover the space existing between the opposing sides of the opening and the compact structure; thus enabling said compact structure to have side movement to make the joining up of the lorry to be loaded or unloaded easier.

According to the invention, the loading wharf on the lower part (running surface of the lorries) has a mechanism that is movable between a folded-up position in which there is a lower space on the inside set out by the compact structure and a projecting position; in its projecting position said mechanism has some means for the detection and blocking of the rear wheels of the lorry during the loading and unloading operations.

In addition and according to the invention in the upper area of the intermediate space the loading wharf has a connection for the supply of a lighting element for the loading and unloading on the inside of the lorry during the loading and unloading operations.

With these stated characteristics, the invention provides some significant technical advantages: The wharf can be supplied pre-installed as an integral module, sized in an appropriate manner for the access opening in which it is to be fitted, and without the need to carry out additional building works as now occurs in the case of the current pits; on closing the outer security door all of the components are hidden behind same, leaving the external façade completely clean; and preventing the build up of dirt and the entry of insects or rodents to the inside of the enclosure; it occupies a minimum space, on taking advantage of the lintel as that provided for the outer walls of the warehouse; it enables the interconnection of all the openings from one to another by means of the connecting of said structures via tubes or pipes through which the pre-installation can be carried out of the electrical, pneumatic and hydraulic supplies in addition to the telephone and data lines; and the problems of the build up of dirt in the area of the installation of the ramp is prevented.

The protective means, in whichever of its variations, has a space which can change its shape in the area of contact with the body of the lorry so as to enable the closure of same.

DESCRIPTION OF THE FIGURES

In order to complete the description that is being made and for the purpose of providing a better understanding of the characteristics of the invention, a set of drawings is attached to this present description in which the figures being by way of illustration and are not by way of limitation on the invention, in which the following is shown.

PREFERRED EMBODIMENT OF THE INVENTION

As and how can be seen in the referenced figures the loading wharf of the present invention includes a compact structure (1) fixed into the surrounding edge of the access opening of the warehouse and which marks out an intermediate space (2), between the inner and outer faces of the wall, for the placement of the sides and the roof of the protective means (4, 5) and the foldable ramp (7).

In the operational position the protective means (4, 5) and the levelling ramp (7) protrude from the intermediate space (2) towards the outside and, in the non-operational position they are arranged in an appreciably vertical manner on the inside of said intermediate space (2).

The compact structure (1) together with the external and internal faces of the wall includes some frames (1a, 1b) for the assembly of an external closure door (3a) on the floor or external level of the warehouse, and an inner door (3b) preferably rapid opening that establishes the closure on the ground level or the inner floor level of the warehouse.

In the operational position of the closure the external door (3a) prevents access to the warehouse or inner enclosure and completely conceals the protective means and the ramp housed in the intermediate space (2) of the loading wharf.

This intermediate space (2) has: A lower area (21) located at ground level outside of the warehouse for the placement of the rear platform (61) of the lorry (6) so that it does not interfere with the wharf during the loading and unloading operations; a lower intermediate area (22) located below the level of the floor on the inside of the warehouse (between the lower area (21) and the inside floor level of the warehouse) for the movement of the platform and the housing of the actioning devices of same, represented in this case by a hydraulic cylinder (72) and the housing (9) where the hydraulic control and the electrical controls are located for the entirety of the system, likewise it is also used for the inter-connection between the differing openings that there may be; an upper intermediate area (23), flush with the inside floor level of the warehouse, for the housing of the sides and roof of the protective means (4, 5) and the levelling ramp (7); and an upper area (24) making the housing for the take up of the external and internal doors (3a, 3b) in the open position by means of some motorised drums.

Figure 1:
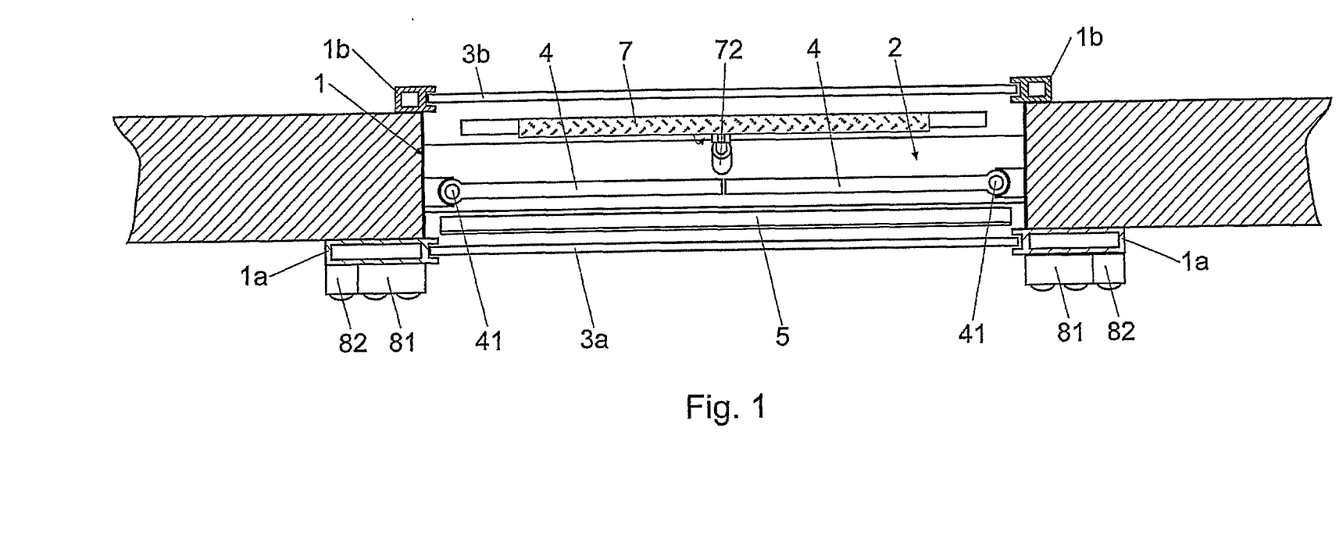
FIG. 1 shows a sectioned plan view of the wharf in a non-operational position.
Figure 2:
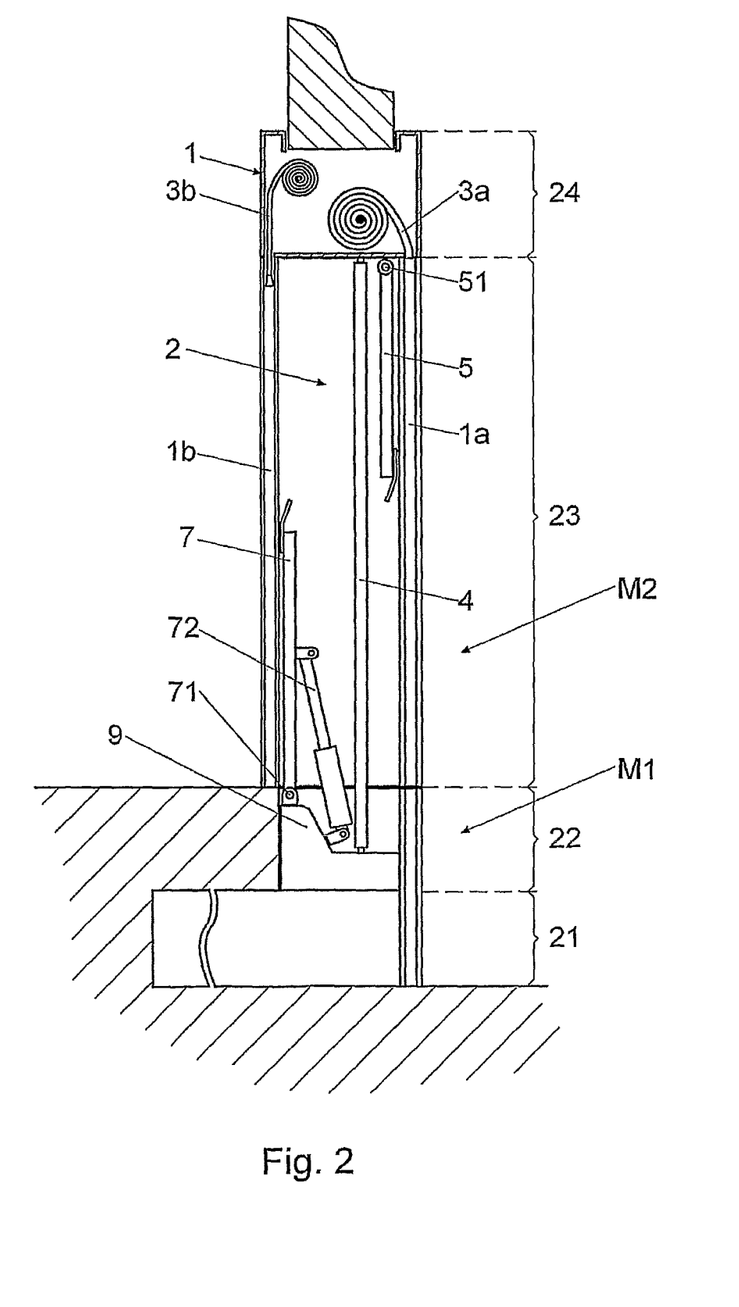
FIG. 2 shows a profile view of the loading wharf in a non-operational position, with the internal and external doors in an open position and sectioned along a vertical plane.

The compact structure (1) can be made up of a single pre-assembled module and that is ready for installation or, as and how shown in FIG. 2, by a lower module (Ml) that takes in the lower level (21) and a lower intermediate area (22), and by an upper module (M2) that takes in the supper intermediate zones (23) and the upper area (24).

Figure 5:
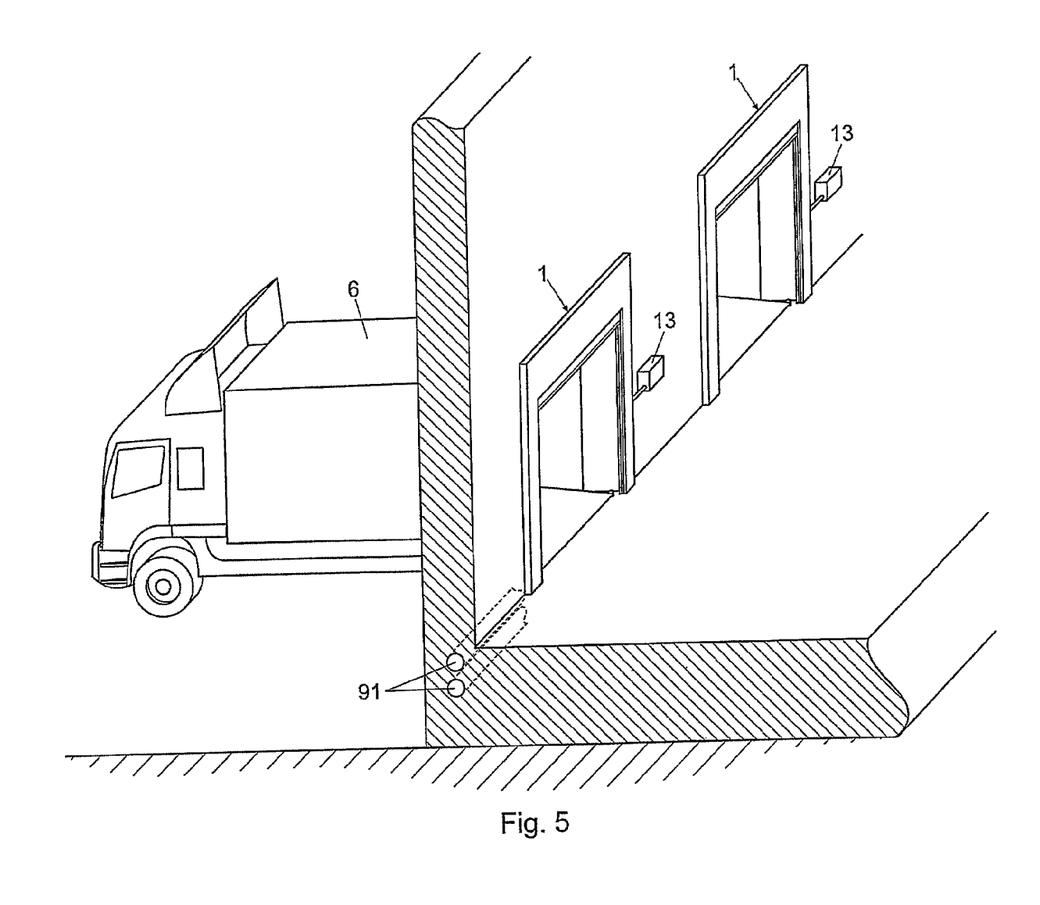
FIG. 5 shows a perspective view of the two loading wharves seen from the inside of the warehouse.-

The successive wharves can be inter-connected by means of built in tubes or pipes (91), shown in FIG. 5, that can join the housings (9) enabling the electrical, pneumatic, telephone and data installations to be made that are necessary for the inter-connection of all of the necessary components in the loading openings meaning that the inner walls remain clean, free of pipes and channelling that could affect or reduce the cleaning of same.

As can be seen in the figures attached, the external and internal frames (1a, 1b) have some channelling for the controls of the doors themselves and the passage of the electrical supply cables and other accessorial services, such as battery chargers (13) shown in FIG. 5, or others, from the control housings (9) fitted in the example shown in the intermediate area (22).

The sides of the protective means (4) are assembled onto both vertical turning axes (41), the roof of the protective means (5) on an upper turning horizontal axis (51) and the ramp (7) on a turning axis (71), which enables same to be appreciably flush with the internal floor level of the warehouse.

In the embodiment shown the upper frame (1a) comprises some means of signalling on the opposing sides so as to make the centring and approach of the vehicle (6) to the wharf easier, said signalling devices being represented, on each side, by two sets of signals (81, 82) forming horizontal and vertical lines.

The horizontal signals (81) are visible with the rear view mirrors, showing the driver if the lorry is correctly centred in regard to the loading wharf whilst the luminous signs (82) of the vertical alignment, of differing colours, are controlled by some sensors integrated into the loading wharf and detect the correct position for the distance or the excessive closeness of the lorry to the loading wharf, the corresponding luminous signal (82) lighting up in a selective manner.

Figure 6:
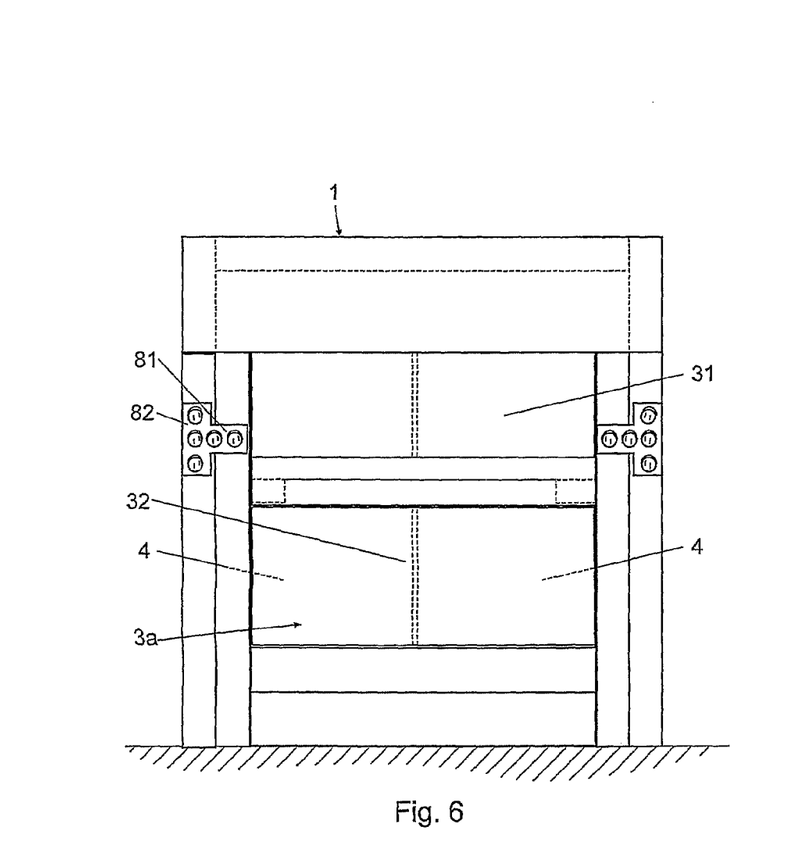
FIG. 6 shows a front elevation view of a variation of an embodiment of the loading wharf in the closed position, in which the external door is made up of two foldable panels, an upper and a lower panel, which in the open position make the roof of the protective means and an additional closure placed in the lower area of the ramp.
Figure 7:
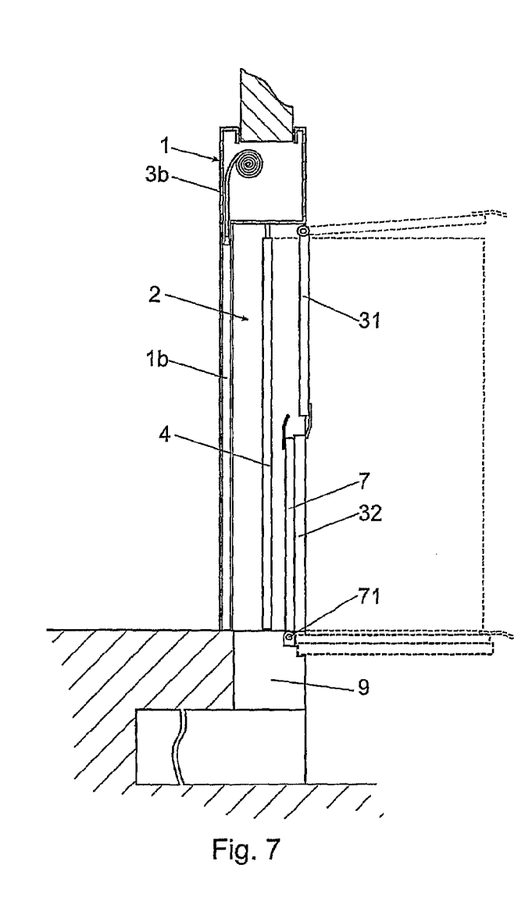
FIG. 7 shows a lateral view of the door of FIG. 6, sectioned along a vertical plane, in which the sides of the protective means of the external door have been represented with an unbroken line in the closed position and a dotted line in the open position.

In the variation of the embodiment shown in FIGS. 6 and 7 the external door (3a) of the wharf includes an upper panel (31) and another lower panel (32) that are foldable on both horizontal axes, said panels making up the corresponding panels of the roof (5) of the protective means and an additional closure flush with the lower area of the ramp (7).

Figure 8:
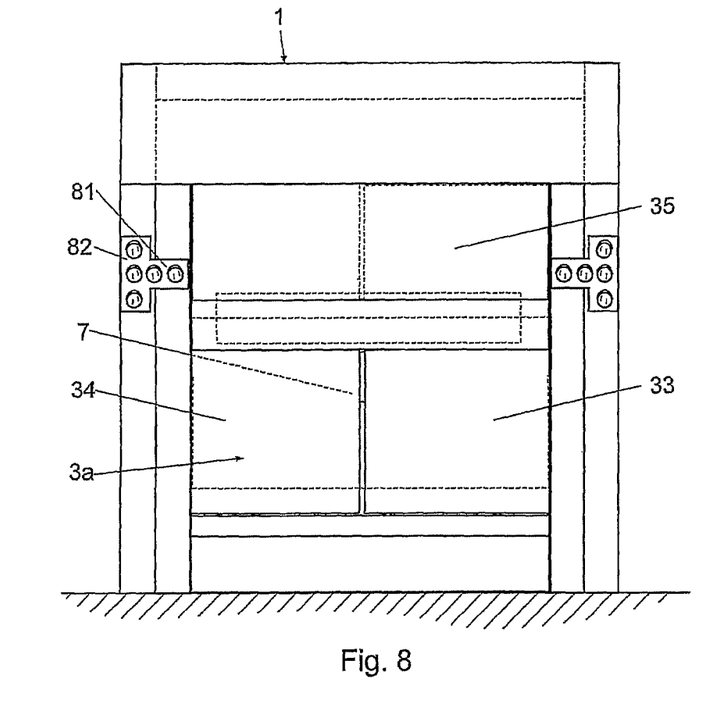
FIG. 8 shows a front elevation view of a variation of an embodiment of the invention of the loading wharf in a closed position, in which the external door is made up from two foldable side panels making the sides of the protective means and an upper foldable cover making up the roof of the protective means.
Figure 9:
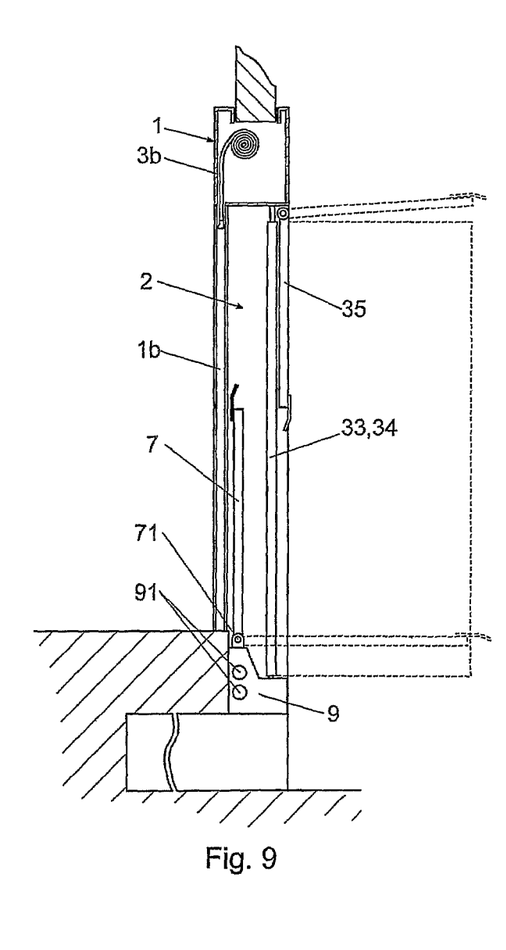
FIG. 9 shows a side view of the door of FIG. 8 sectioned along a vertical plane and where the external door and the ramp in the closed position have been represented by an unbroken line and the unfolded position by a dotted line.

In the variation of the embodiment shown in FIGS. 8 and 9, the external door (3a) is made up of two side panels (33, 34) that are foldable on both vertical axes, that make the sides (4) of the protective means in the unfolded position, and by an upper cover (35) that is foldable on a horizontal axis, which makes the roof of the protective means (5) in the unfolded position.

Figure 10:
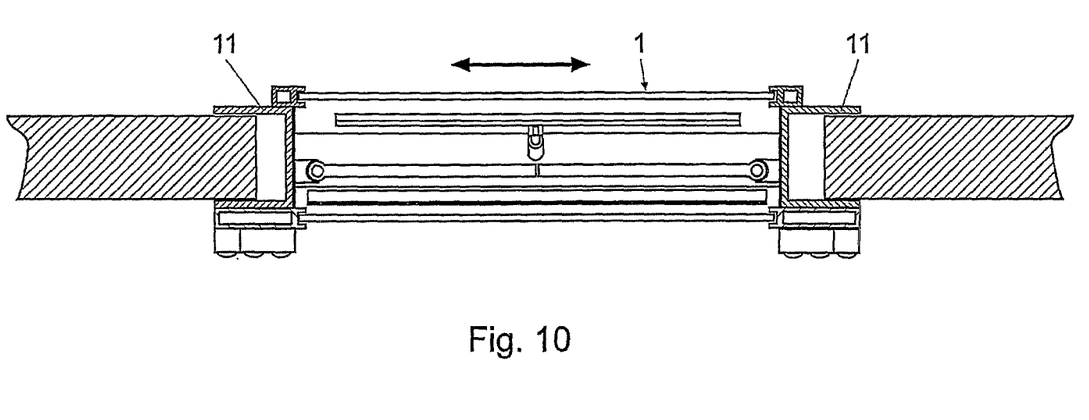
FIG. 10 shows an upper plan view of a variation of an embodiment of the loading wharf, sectioned along a horizontal plane, in which the compact structure has a smaller width than the warehouse opening, and has some lateral projections that fully cover the space that there is between the opposing sides of the opening and the compact structure; said compact structure thus being able to have lateral movement to make the coupling up of the lorry easier.

In the example of the embodiment shown in FIG. 10, the compact structure (1) has a smaller width than the warehouse access opening, and has some side projections (11) that fully cover the space existing between the opposing sides of the opening and the compact structure (1); thus said structure (1) is able to easily make the alignment and coupling with the lorry to be loaded or unloaded.

Figure 3A:
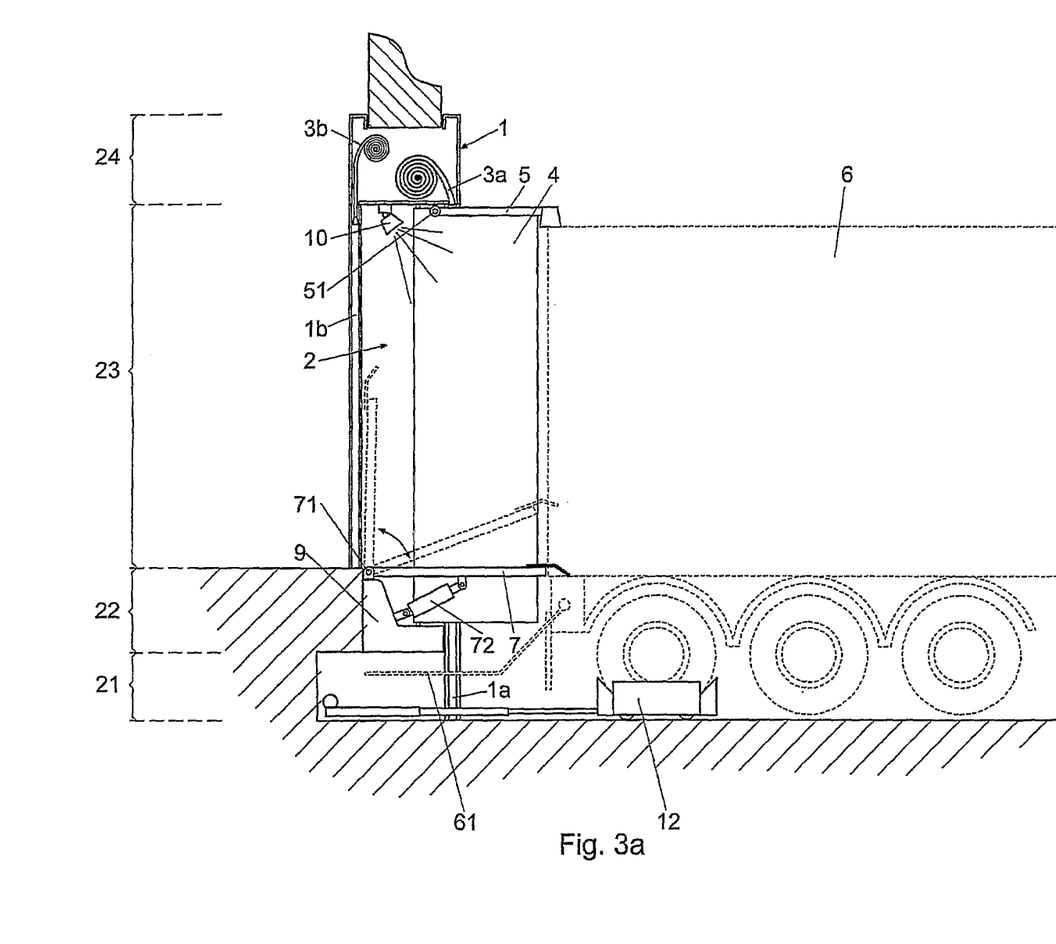
FIG. 3a shows a sectioned profile view of the loading wharf sectioned along a vertical plane and in an operational position.
Figure 3B:
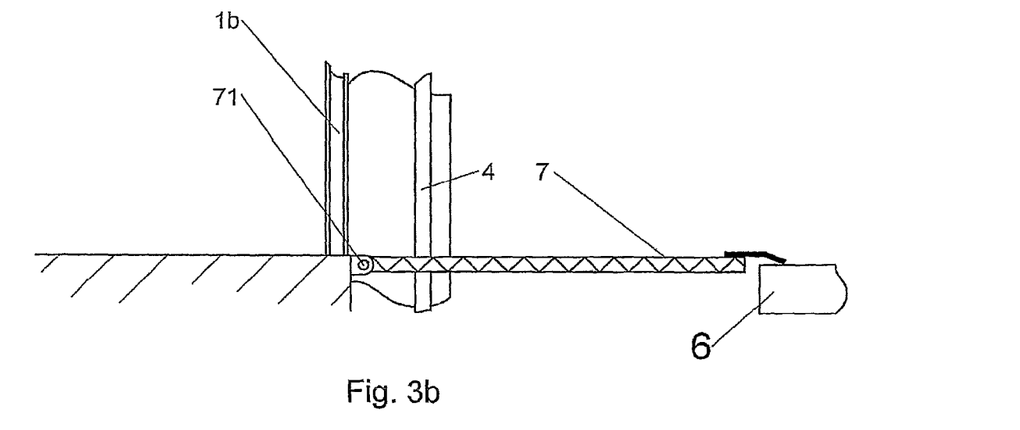
FIG. 3b shows an expanded detail of the previous figure in which a constructive form of the ramp can be seen, arranged in an operational position and supported on the body of the lorry.
Figure 4:
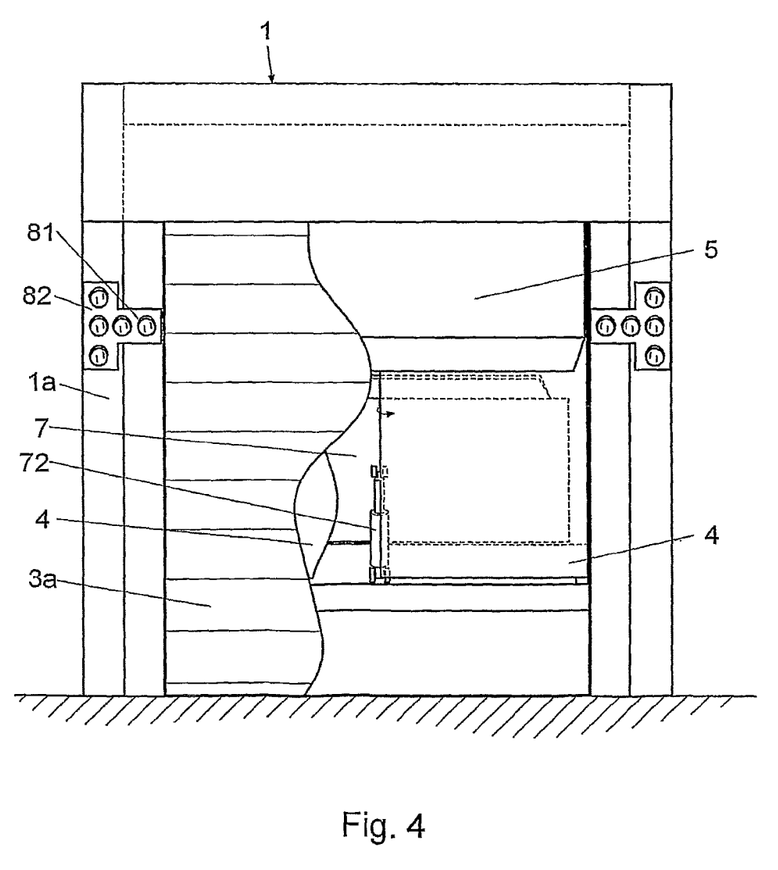
FIG. 4 shows an elevation view of the loading wharf in a non-operational position with the external door closed and partially sectioned.

In the example of the embodiment shown in FIG. 3a, the loading wharf has a mechanism (12) in the lower space (21)

that is movable between the folded up position in which in the lower space (21) marked out by the compact structure, and a protruding position; said mechanism has some means for the detection and blocking of the rear wheels of the lorry (6) during the loading and unloading operations in its protruding position.

In the embodiment shown in said FIG. 3a, on the upper area of the intermediate space (23) the loading wharf has a connection (10) for the supply of a lighting element for the loading and unloading area and for the inside of the lorry (6) during the loading and unloading operations.

Figure 11:
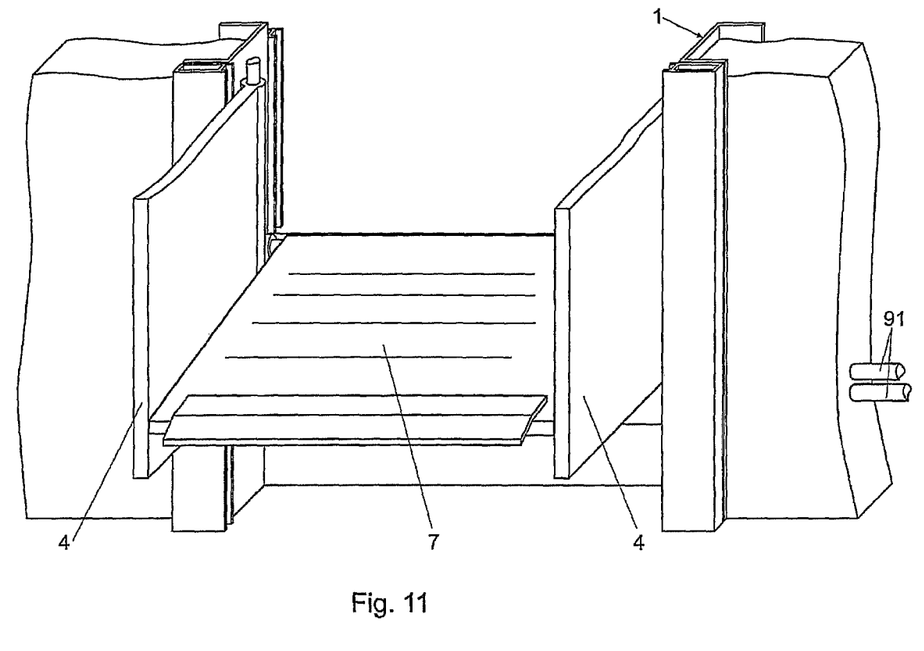
FIG. 11 shows a detail in perspective of the sides of the protective means in the operating position, making contact with the opposing sides of the ramp.

As can be seen in FIG. 11, in the operational position the sides of the protective means (4) make contact with the opposing sides of the ramp (7) preventing the existence of intermediate spaces and they are inter-connected with the ramp (7) actioning the protective means and the ramp as one unit that is adjusted in height to the support surface on the inside of the lorry, preventing rubbing between the body of the lorry and the sides (4) of the protective means.

Once having sufficiently described the nature of the invention, likewise having given an example of a preferred embodiment it is placed on record that the materials, shape, size and arrangement of the elements described can be modified provided that they do not mean an alteration of the basic essentials of the invention that are claimed below.

The invention claimed is:

1. A loading wharf for attachment to a building to define a passageway between the building and a trailer body of a vehicle, the loading wharf comprising:
a main structure that is received within an access opening formed in a wall of the building and is fixedly attached to the wall, the access opening being defined by a plurality of inner wall surfaces that lie between internal and external faces of the wall of the building, the access opening defining an intermediate space between the internal and external faces of the wall of the building, wherein the main structure includes a first frame member for connection to the internal faces of the wall and a second frame member for connection to the external faces of the wall for securing the main structure to the wall;
an external closure door assembly that is coupled to the second frame member and is disposed above a ground surface external to the building, wherein the external closure door assembly includes an external door;
an internal door assembly that is coupled to the first frame member and is positioned for establishing a closure on an inner floor of the building which lies above the ground surface, wherein the internal closure door assembly includes an internal door;
a folding levelling ramp that is disposed within the intermediate space and forms the passageway between the building and the trailer body of the vehicle;
first and second protective members that are disposed within the intermediate space and are for protection of side and upper spaces defined between the building and the trailer body of the vehicle during loading and unloading operations;
wherein the folding levelling ramp and the first and second protective members are positioned between an operational position and a non-operational position,
wherein in the operational position, the folding levelling ramp and the first and second protective members project from the intermediate space towards an outside of the building so as to interact with the trailer body of the vehicle to be loaded or unloaded, and wherein in the non-operational position, the folding levelling ramp and the first and second protective members are disposed and contained within the intermediate space.

2. Loading wharf, according to claim 1, wherein the intermediate space has: (1) a lower area located at the ground surface external to the building for the housing of a rear platform of the vehicle of the or safety mechanisms intended to prevent the movement of the vehicle during the loading and unloading operations, (2) a lower intermediate area located below the inner floor of the building for: (a) the actioning and movement of the levelling ramp, (b) electric control mechanisms and interconnection devices between a plurality of wharves, (c) an upper intermediate area, flush with the inner floor of the building, for main structure containing the protective means and the levelling platform, and (d) an upper area making a housing for take up of the external and internal doors in an open position or the placement of the interconnection devices and the controls associated therewith.

3. Loading wharf, according to claim 1, wherein the main structure is made up from a single pre-assembled module, that extends from the ground surface external to the building to a top edge of the access opening.

4. Loading wharf, according to claim 1, wherein the main structure is made up from two separate modules: (a) a lower module (M1) that occupies the lower area and the lower intermediate area, and by an upper module (M2) that occupies the upper intermediate area and the upper area.

5. Loading wharf according to claim 1, wherein the first and second frame members include channelling for receiving controls of the internal and external doors and for passage of electrical supply cables, signalling elements, lighting switches or other means of communication.

6. Loading wharf according to claim 1, wherein the first and second protective members are made up of two side wall structures and an upper folding roof.

7. Loading wharf according to claim 6, wherein the side wall structures are both assembled on vertical turning axes to allow the side wall structures to pivot about said axes, next to and extending vertically along inner surfaces of the main structure.

8. Loading wharf according to claim 6, wherein the upper folding roof is assembled on a horizontal turning axis that extends horizontally cross the main structure, the upper folding roof pivoting about the horizontal turning axis.

9. Loading wharf according to claim 1, wherein the folding levelling ramp pivots about an axis.

10. Loading wharf according to claim 6, wherein in the non-operational position the side wall structures, the upper folding roof and the folding levelling ramp are fitted in a vertical manner within the intermediate space outlined by the external and internal doors and by the main structure.

11. Loading wharf according to claim 1, the second frame member has signalling devices on opposing sides thereof to assist in vehicle centering and approach to the loading wharf and that on each side of the wharf there are two sets of signals for horizontal and vertical alignment of the vehicle.

12. Loading wharf according to claim 1, wherein in the operational position the folding levelling ramp and the first and second protective members form a unit that is adapted to variations in height brought about to a support surface of the folding levelling ramp on the inside of the vehicle during the loading and unloading operations, due to weight variations of a load, preventing rubbing between the first and second protective members and the vehicle.

13. Loading wharf according to claim 1, wherein successive wharves can be inter-connected by means of built in tubes or pipes that can join housings that contain working components of the loading wharf enabling electrical, pneumatic, telephone and data installations to be made that are necessary for the inter-connection of selected working components in the access openings resulting in inner walls remaining clean, free of pipes and channelling that affect or reduce cleaning of the same.

14. Loading wharf according to claim 1, wherein the external door has an upper and lower panel, both foldable on horizontal axes, said upper and lower panels respectively defining a roof of the first and second protective members and an additional closure flush with an inner area of the folding levelling ramp.

15. Loading wharf according to claim 6, wherein the external door is made up of two foldable side panels that in an unfolded position form the side panels (4) of the protective means, and by an upper foldable panel that forms the upper folding roof in the unfolded position.

16. Loading wharf according to claim 1, wherein the main structure has enough space to allow it to move sideways on axes so as to be able to link up to the vehicle.

17. Loading wharf according to claim 1, further including a moveable mechanism on the lower area between the folded up position which is provided on the inside of the lower space and a projecting position; said moveable mechanism having devices for the detection and blocking, in its projecting position, of rear wheels of the vehicle during the loading and unloading operations.

18. Loading wharf according to claim 1, further including a connection for supply of a lighting element in the intermediate space of the loading and unloading area and an inside of the vehicle during the loading and unloading operations.

19. Loading wharf according to claim 1, wherein the folding levelling ramp, with the exception of a toe thereof, has the same width as an internal space of sides of the first and second protective members for minimising openings that are between an outside and an inside of the building.

20. Loading wharf according to claim 1, wherein the first and second protective members has a space that loses its shape in a contact area with the trailer body of the vehicle that allows for the closure of the first and second protective members.

21. A loading wharf for attachment to a building to define a passageway between the building and a trailer body of a vehicle, the loading wharf comprising:
a main structure that is received within an access opening formed in a wall of the building and is fixedly attached to the wall, the access opening being defined by a plurality of inner wall surfaces that lie between internal and external faces of the wall of the building, the access opening defining an intermediate space between the internal and external faces of the wall of the building, wherein the main structure includes a first frame member for connection to the internal faces of the wall and a second frame member for connection to the external faces of the wall for securing the main structure to the wall;
an external closure door assembly that is coupled to the second frame member and is disposed above a ground surface external to the building, wherein the external closure door assembly includes an external door that travels within a channel formed in the second frame member;
an internal door assembly that is coupled to the first frame member and is positioned for establishing a closure on an inner floor of the building which lies above the ground surface, wherein the internal closure door assembly includes an internal door that travels within a channel formed in the first frame member;
a folding levelling ramp that is disposed within the intermediate space and forms the passageway between the building and the trailer body of the vehicle;
first and second protective members that are disposed within the intermediate space between the first and second frame members and are for protection of side and upper spaces, respectively, defined between the building and the trailer body of the vehicle during loading and unloading operations, wherein the first protective member comprises a pair of side wall structures that pivot about a pair of vertical oriented axes and the second protective member comprises an upper folding roof that pivots about an upper horizontal axis located along a top of the intermediate space;
wherein the folding levelling ramp and the side walls structures and upper folding roof are positioned between an operational position and a non-operational position,
wherein in the operational position, the folding levelling ramp and the side walls structures and upper folding roof project outwardly from the intermediate space such that the side walls structures and upper folding roof extend beyond the external face of the wall of the building so as to interact with the trailer body of the vehicle to be loaded or unloaded, and wherein in the non-operational position, the folding levelling ramp and the side walls structures and upper folding roof are disposed and contained within the intermediate space.

* * * * *